Feb. 1, 1966 M. L. MEILLAND Plant Pat. 2,598
ROSE PLANT
Filed Dec. 7, 1964
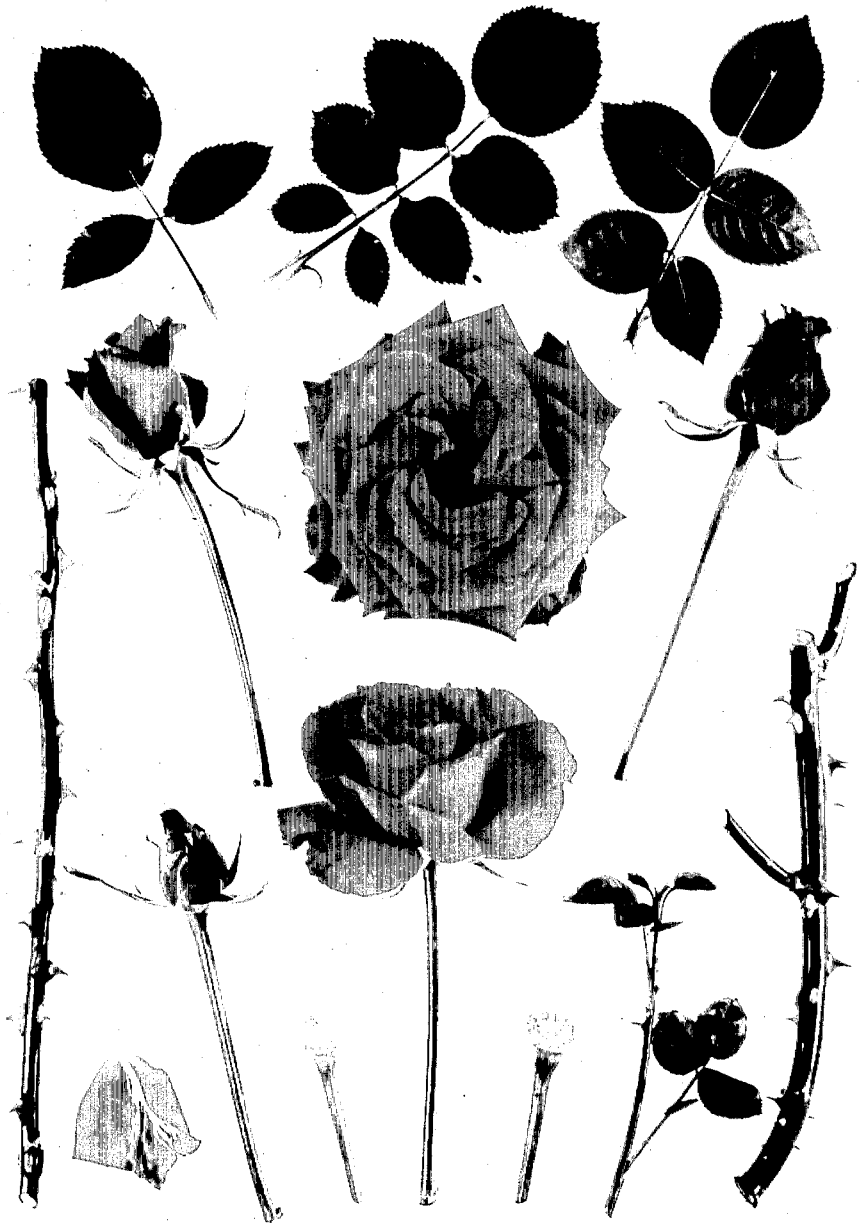
Inventor.
Marie Louise Meilland
By: Robert Robb
Attorneys.

United States Patent Office

Plant Pat. 2,598
Patented Feb. 1, 1966

2,598
ROSE PLANT

Marie Louise Meilland, Alpes Maritimes, France, assignor to The Conard-Pyle Company, West Grove, Pa., a corporation of Pennsylvania Filed Dec. 7, 1964, Ser. No. 416,661
Claims priority, application France, Jan. 27, 1964, 44,398
1 Claim. (Cl. Plt.—20)

The present invention relates to a new and distinct variety of rose plant of the hybrid tea class, which was originated by me by crossing the variety known as "Baccara" (U.S. Plant Patent No. 1,367) with an unnamed and unpatented seedling derived from a cross of the variety "Independence," known in Europe as "Kordes Sondermeldung" (U.S. Plant Patent No. 1,036) × "Peace," known in France as "Mme. A. Meilland" (U.S. Plant Patent No. 591).

The primary objective of this breeding was to produce a new rose variety which bears flowers of a clearer and brighter red color than the flowers of the variety known as "Happiness," known in Europe as "Rouge Meilland" (U.S. Plant Patent No. 911), and which is suitable for commercial needs of the horticultural industry, as well as being at least as productive as the parent variety "Baccara," with a cut flower longevity at least as great as or greater than that of "Baccara." This objective was fully achieved, along with other desirable improvements, as evidenced by the following unique combination of characteristics which are outstanding in the new variety and which distinguish it from its parents, as well as from all other varieties of which I am aware:

(1) An upright and vigorous habit of growth;
(2) A free-blooming and abundantly recurrent habit;
(3) A double flower form, with firm petals arranged in an open shape with a high center, but becoming more rounded and with the petals overlapping about the outer periphery;
(4) A distinctive and attractive flower color corresponding to Cherry Red on the outside of the petals and velvety Cardinal Red on the inside of the petals;
(5) A long-lasting quality of the flowers as cut flowers;
(6) A clean dropping habit of the flowers; and
(7) Very good resistance to blackspot, downy mildew, powdery mildew and rust.

Asexual reproduction of the new variety by budding, as performed in France and also at West Grove, Pennsylvania, U.S.A., shows that the foregoing characteristics and distinctions come true to form and are established and transmitted through succeeding propagations.

The accompanying drawing shows typical specimens of the vegetative growth and flowers of my new variety in different steps of development and as depicted in color as nearly true as it is reasonably possible to make the same in a color illustration of this character.

The following is a detailed description of the new variety, with color terminology in accordance with the Horticultural Colour Chart of the Royal Horticultural Society, except where general color terms of ordinary dictionary significance are obvious:

Type: Hardy; bush; greenhouse; seedling; for cut flowers.
Class: Hybrid tea.
Breeding: Seedling.
*Seed parent.*—"Baccara."
*Pollen parent.*—An unnamed seedling of "Independence" × "Peace."
Propagation: Holds its distinguishing characteristics through succeeding propagations by budding.

*Flower*

Locality where grown and observed: Cap d'Antibes, France.
Flowers borne: Usually singly to stem; on long stems of normal strength.
Quantity of bloom: Free and abundant in greenhouse.
Continuity: Continuous.
Fragrance: None.
Bud:
*Peduncle.*—Medium length; medium caliper; very stiff; smooth.
*Before calyx breaks.*—Size—medium. Form—pointed; with foliaceous appendages on the surface of the bud.
*As calyx breaks.*—Color—Dull Cardinal Red, Plate 822, more or less spotted with Maroon, Plate 1030/3.
*As first petal opens.*—Size—medium. Form—truncate. Color: Outside—Cherry Red, Plate 722, shaded with velvety Cardinal Red, Plate 822; inside—Dull Cardinal Red, Plate 822/3.
*Opening.*—Opens up well.
Bloom:
*Size (when fully open).*—Large; from about 11 cm. to 13 cm.
*Petalage.*—Double; from 30 to 35 petals.
*Form.*—Open and high-centered at first, but becoming cupped; petals at first being loosely rolled outward and remaining loosely rolled outward at maturity.
Petals:
*Texture.*—Very firm.
*Shape.*—Outer—obovate. Intermediate—obovate. Inner—irregular.

This description was made from a rose grown in a greenhouse at Cap d'Antibes, France:

*Color.*—Outside petal surface—Bright Cherry Red, Plate 722, shaded with velvety Cardinal Red, Plate 822/3 on opening, but becoming generally Cherry Red, Plate 722, when fully open. Inside petal surface—Dull Cardinal Red, Plate 822/3 on opening, and remaining generally Cardinal Red, Plate 822/3 when fully open.

This description was made from a rose that was open for three days in a greenhouse at Cap d'Antibes, France:

*Color.*—Outside petal surface—Cherry Red, Plate 722. Inside petal surface—Cardinal Red, Plate 822/3.
*General color effect.*—Newly opened flower—Cherry Red, Plate 722, with reverse of petals Cardinal Red, Plate 822/3. 3-days open—Cherry Red, Plate 722, with reverse of petals Cardinal Red, Plate 822/3.
*Behavior.*—Drop off cleanly.
*Flower longevity.*—Very long.

*Reproductive organs*

Stamens: Many.
Filaments: Medium length. Color—reddish.
Anthers: Color—pale yellow.
Pistils: Many.
Styles: Uneven.
Stigma: Color—yellowish.
Ovaries: Some protruding from receptacle.
Hips: None observed.
Sepals: Short; narrow.
Seeds: None observed.

*Plant*

Foliage:

*Leaves.*—Compound of 3, 5 or 7 leaflets; moderately large size.

*Leaflets.*—Many. Shape—elliptical. Margin—irregularly serrate.

*Color.*—Mature: Upper surface—Spinach Green, Plate 0960; under surface—Spinach Green, Plate 0960/3.

*Rachis (the supporting stem of the compound leaf).*—Upper side—sometimes smooth. Under side—sparsely prickly.

*Stipules.*—Short; narrow; with moderately long points.

*Disease resistance.*—Very good resistance to blackspot, downy mildew, powdery mildew and rust, as determined by comparison of other varieties grown under comparable cultural conditions at Cap d'Antibes, France.

Growth:

*Habit.*—Upright; much-branched.

*Growth.*—Free; vigorous.

*Main stems.*—Color—Spinach Green, Plate 0960. Prickles—normal quantity; medium size; straight; narrow; color—snuff brown.

*Branches.*—Color—Spinach Green, Plate 0960/1, washed with Lettuce Green, Plate 861/1.

*New shoots.*—Color—Lettuce Green, Plate 861/1, overlaid with reddish brown.

I claim:

A new and distinct variety of rose plant of the hybrid tea class, substantially as herein shown and described, characterized particularly as to novelty by the unique combination of an upright and vigorous habit of growth, a free-blooming and abundantly recurrent habit, a double flower form, with firm petals arranged in an open shape with a high center, but becoming more rounded and with the petals overlapping about the outer periphery, a distinctive and attractive flower color corresponding to Cherry Red on the outside of the petals and valvety Cardinal Red on the inside of the petals, a long-lasting quality of the flowers as cut flowers, a clean dropping habit of the flowers, and very good resistance to blackspot, downy mildew, powdery mildew and rust.

No references cited.

ABRAHAM G. STONE, *Primary Examiner.*

R. E. BAGWILL, *Assistant Examiner.*